United States Patent [19]

Mack et al.

[11] 4,140,488

[45] Feb. 20, 1979

[54] SAMPLE LIQUID TRANSFER MEANS IN AN AUTOMATIC CHEMICAL TESTING APPARATUS

[75] Inventors: Daniel R. Mack; James R. Eseke, both of Houston, Tex.

[73] Assignee: Hycel, Inc., Houston, Tex.

[21] Appl. No.: 830,705

[22] Filed: Sep. 6, 1977

[51] Int. Cl.$^{2}$ .......................... B01L 3/02; G01N 1/14; G01N 31/00

[52] U.S. Cl. ....................................... 422/100; 73/425; 222/309; 141/21; 422/50

[58] Field of Search ............. 23/259, 253 R; 222/148, 222/309; 73/425.4 P, 425.6; 128/214.4, 218 P

[56] References Cited

U.S. PATENT DOCUMENTS

| | | | |
|---|---|---|---|
| 3,252,330 | 5/1966 | Kling | 23/253 R |
| 3,723,066 | 3/1973 | Moran | 23/259 X |
| 3,815,790 | 6/1974 | Allen et al. | 73/425.6 |
| 3,900,289 | 8/1975 | Liston | 23/253 R |
| 4,023,716 | 5/1977 | Shapiro | 222/309 |
| 4,039,287 | 8/1977 | Moran | 23/259 X |
| 4,039,288 | 8/1977 | Moran | 23/253 R |

*Primary Examiner*—Morris O. Wolk
*Assistant Examiner*—Michael S. Marcus
*Attorney, Agent, or Firm*—Timothy L. Burgess; Robert P. Cogan

[57] ABSTRACT

Means for reducing intersample contamination in an automatic chemical testing apparatus, in which liquid from a sample is aspirated from a sample source into a reservoir, and aliquots of the sample are each dispensed into individual reaction containers for analysis by well-known means. A cylindrical reservoir is utilized with a piston therein shaped for pushing out virtually all of the remaining sample from the cylinder after dispensing the sample liquid through a hollow needle, communicating with the cylinder. A solid pin coaxially mounted within the piston is projected through the needle and has minimum clearance therewith, for pushing remaining sample out of the needle. The portion of the pin projecting through the needle is retracted into the piston prior to aspiration of liquid from a next sample.

19 Claims, 7 Drawing Figures 55 56 57 61 46 51 48 52 47 59 39 38 40 44 41 42 31 43 30 32 33 36

38
36
30

38
36
41
32
36
47

63
46
30
36

SAMPLE LIQUID TRANSFER MEANS IN AN AUTOMATIC CHEMICAL TESTING APPARATUS

BACKGROUND OF THE INVENTION

The present invention relates to automated apparatus for chemical testing of liquid samples to determine concentrations of substances therein, and more particularly to an improvement in liquid transfer means included therein.

The present invention is an improvement in chemical analyzers of the type in which sample liquid is taken from a sample container and aliquots thereof are each placed in one or more reaction containers. Reagents are added to each reaction container. A resulting reaction mixture is incubated, and then spectrophotometrically measured to indicate concentrations of substances in the samples for which the analysis is being conducted. In the preferred form, the present invention is included in a blood serum analyzer. An example of an automatic chemical testing apparatus of the sort contemplated by the present invention, is shown in U.S. Pat. Nos. 3,622,279 and 3,716,338, both to John J. Moran, and respectively issued on Nov. 23, 1971 and Feb. 13, 1973. These patents are commonly assigned to the assignee herein, and their disclosures are incorporated herein by reference.

In such chemical analyzers, sample liquid such as blood serum is provided in a source, such as a sample cup, and must be transferred to reaction containers. The same transfer means are used to transfer an amount of sample liquid from each of a number of successive samples to respective successive sets of reaction containers. If liquid remaining in the transfer means from a first sample is mixed with a next sample, intersample contamination, commonly referred to as carryover, may result.

Various prior art schemes have provided for transfer means which are subject to carryover. Common prior arrangements utilize pumping of sample liquid through tubes extending from a sample station to a reaction station. The transfer means in the above-cited patents to Moran is an improvement over those earlier forms of transfer means in that sample liquid is aspirated into a reservoir, and the reservoir is moved to reaction containers and becomes the dispensing means. The hydraulic pathlength through which the sample must travel is thus reduced, and far less surface area on the interior of conduits is provided on which sample liquid may remain. Further, efficient washing means are provided in the aspiration-dispensing means to guard against carryover.

The present invention comprehends further improvements in the transfer means for further improved reduction of carryover by positive displacement of sample liquid from the transfer means.

SUMMARY OF THE INVENTION

It is therefore an object of the present invention to provide liquid transfer means in an automatic chemical testing apparatus of the type in which liquid sample is aspirated into a reservoir and dispensed therefrom in which mechanical means for reducing carryover are provided.

It is a further object of the present invention to provide a transfer means of the type described in which a conduit having a first end at a reservoir and a second end comprising an aspiration-dispense inlet-outlet is cleared by moving a solid member therethrough between successive transfer cycles.

It is also an object of the present invention to provide a transfer means of the type described wherein said reservoir comprises a cylinder in which a piston is operated to displace substantially all fluid from the reservoir during the transfer cycle.

It is a further object in one form of the present invention to provide a transfer means of the type described in which said solid displacement means is incorporated in an operating mechanism with the piston.

It is also a general object of the present invention to provide a transfer station of the type described in which the ability to eliminate the step of washing for eliminating carryover is facilitated.

Briefly stated, in accordance with the present invention, there is provided in an automatic chemical testing apparatus a sample liquid transfer station comprising a reservoir and liquid pumping means, preferably a cylinder and a piston. A conduit, preferably in the form of a hollow needle, has a first end communicating with the reservoir and an opposite end serving as an inlet-outlet. A liquid displacement means is mounted for movement preferably through the pumping means, and is operated between transfers of liquid from successive samples to project to displace fluid from the conduit. Preferably, the pumping means is operated to displace all fluid from the reservoir.

BRIEF DESCRIPTION OF THE DRAWINGS

The means by which the foregoing objects and features of invention are achieved are pointed out with particularity in the claims forming the concluding portion of the specification. The invention, both as to its organization and manner of operation, may be further understood by reference to the following description taken in connection with the following drawings. Of the Drawings:

DESCRIPTION OF THE PREFERRED EMBODIMENT

Figure 1:
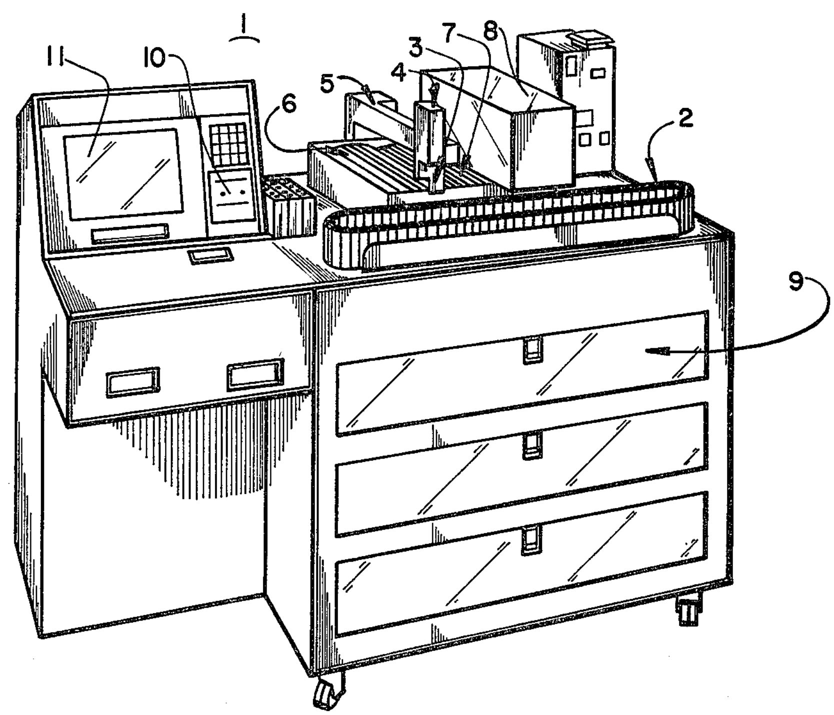
FIG. 1 is an illustration of an automatic chemical testing appratus which may incorporate the present invention.

Referring to FIG. 1, there is illustrated an automatic chemical testing apparatus 1 such as that described in the above-cited patents to Moran. The apparatus 1 is briefly described, prior to a detailed description of the subject sample liquid transfer means. Samples are provided in individual containers in a sample conveyor 2 to an aspiration station 3. The analyzer 1 and sample conveyor 2 are further illustrated in commonly assigned U.S. Pat. No. 4,039,288 issued Aug. 2, 1977 to John J. Moran, the disclosure of which is incorporated herein by reference. A sample liquid transfer means 4 (also called the transfer means 4 for conciseness in description), such as that of the present invention, operates to withdraw a preselected amount of sample liquid from a sample at the aspiration station 3. At a serum dispensing station 5, aliquots of the sample liquid are dispensed to rows 6 of reaction containers from the transfer means 4. The rows 6 are indexed through a reaction means 7. The reaction means 7 includes means for incubation and reagent dispensing means which add reagent to the sample aliquots. The reagents react with each sample aliquot to form reaction mixtures. The reaction mixtures are analyzed, preferably spectrophotometrically, at an analysis station 8. Reagents are supplied to the reaction means 7, from reagent bottles in a reagent source system 9. Chemical tests may be selected by a control means 10, and test results may be provided at a terminal 11 which may include a CRT display and additionally or alternatively may include means for providing hard copy printouts.

Figure 2:
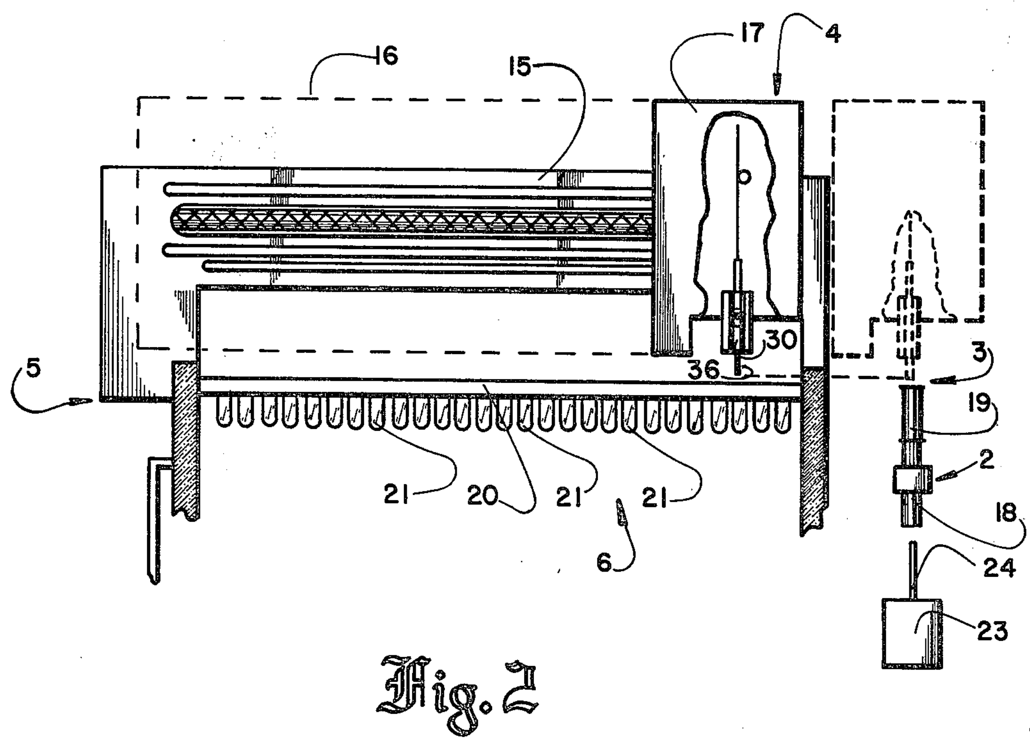
FIG. 2 is a partial side elevation view of the apparatus of FIG. 1 illustrating a sample liquid transfer means of the present invention and a row of reaction containers for receiving aliquots of a sample.

FIG. 2 is a partial side elevation of the apparatus of FIG. 1 illustrating the aspiration station 3, the sample liquid transfer means 4 of the present invention, dispensing station 5, and partially illustrating the sample conveyor 2 and one row 6 of reaction containers positioned at the dispensing station 5.

In the embodiment of FIG. 2, the transfer means 4 comprises a housing 17, illustrated partially broken away, supported on an arm 15 including motive means for transporting the transfer means 4 from the position in which the transfer means 4 is shown in dotted lines at the aspiration station 3 and through a path for dispensing aliquots of a sample. The area 16 in FIG. 2 in dotted lines indicates the extent of travel of the transfer means 4 at the dispensing station 5. Operation of the apparatus and the dispensing station 5 is further described in commonly assigned patent application Ser. No. 725,270 filed Sept. 21, 1976 by John J. Moran, the disclosure of which is also incorporated by reference herein.

The sample conveyor 2 includes a plurality of sample container holders 18, linked together to form the sample conveyor 2 and each holding a sample container 19. Each row 6 comprises a slat 20 holding a plurality of reaction containers 21. A plurality of slats 20 are preferably provided in a loop conveyor such as that disclosed in commonly assigned U.S. Pat. No. 4,039,287 issued Aug. 2, 1977 to John J. Moran, the disclosure of which is also incorporated by reference herein. In such an embodiment, the slats 20 are indexed to successive positions to carry reaction containers 21 from the dispensing station 5 through the reaction means 7 to the analysis station 8.

A sample container displacement unit 23 is provided for periodically moving successive ones of the sample containers 19 in registration with the transfer means 4 for aspiration of sample liquid therefrom. In the present embodiment, the transfer means 4 remains vertically fixed, and is horizontally movable. Therefore, to provide relative motion between a sample container 19 and the transfer means 4, the sample container displacement means 23 includes a vertically movable rod 24 for projecting through an opening in a sample container holder 18 for providing relative motion between the transfer means 4 and the sample container 19 in registration therewith.

Figure 3:
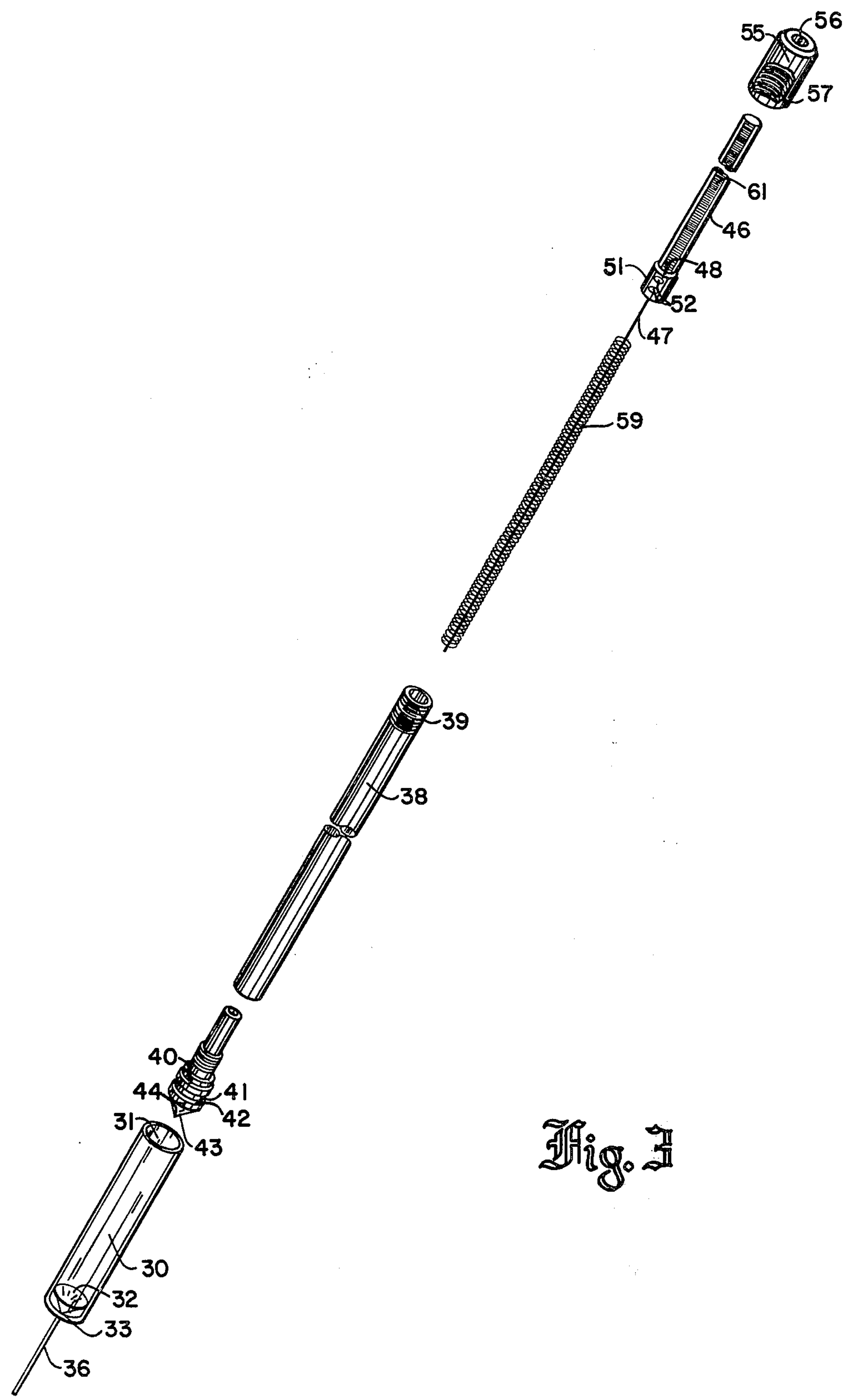
FIG. 3 is an exploded view of components of the sample liquid transfer apparatus constructed in accordance with the present invention.
Figure 4:
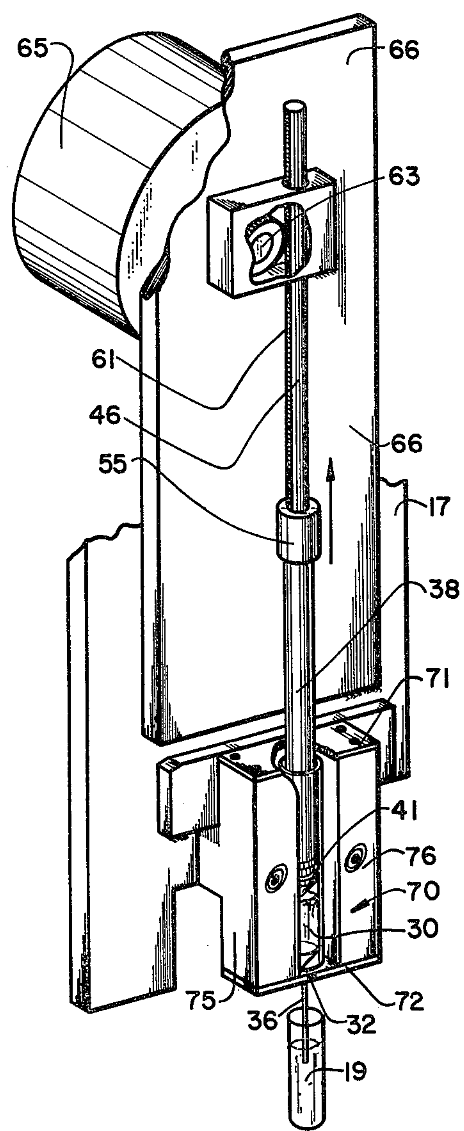
FIGS. 4–7 are illustrations of the sample liquid transfer apparatus of the present invention useful in understanding the structure and operation thereof.

The transfer means 4 is further described with respect to FIG. 2, with respect to FIG. 3, which is an exploded view of components within the transfer means 4, and with respect to FIG. 4 which is an axonometric view illustrating in further detail the structure of the transfer means 4.

A cylinder 30 serves as a reservoir for sample liquid, and is mounted to the housing 17. The cylinder 30 may take many different shapes, but is most conveniently a right circular cylinder and may be made of glass or of a polymer. The cylinder 30 has an opening 31 at an upper end thereof and seating means 32 closing a lower end thereof. It should be remembered that the terms upper and lower are used for defining relative spatial relationships. While it is certainly preferable that the cylinder 30 be vertically disposed, it is not an absolute necessity. The seating means 32 includes an aperture 33 for communication of the interior of the cylinder 30 with a fluid path. A conduit is provided in the form of a hollow needle 36 having an upper end received in the aperture 33 and a lower, open end for intake of sample liquid during aspiration and for expelling sample liquid during dispensing.

In order to provide for aspiration and dispensing of sample liquid into and out of the cylinder 30, pumping means are provided in the form of a piston 38. The piston 38 has an upper end 39 and a lower end 40. The piston 38 is received into the cylinder 30 through the opening 31. The lower end 40 is shaped to mate with the seating means 32. Preferably, the piston 38 is stainless steel, and the lower end 40 comprises a separate, lower polymeric member 41 having an annular recess 42 on its periphery and a conical projection 43 at its lower end. Preferably the seating-means 32 comprises a conical seat for receiving the lower end 40. The purpose of this construction is to provide for substantial total elimination of dead volume, i.e. volume of sample remaining in the cylinder 30 at the completion of downward travel of the piston 38. The annular recess 42 provides for improved fit of the member 41 in the cylinder 30, reduces friction and improves sealing. The lower member 41 has an aperture 44 formed in registration with the aperture 33 in the seating means 32. The aperture 44 extends axially through the lower member 41 to communicate with the interior of the piston 38, which is hollow and has an inner diameter sufficient for receiving components described below.

It is also desired to provide for elimination of dead volume in the needle 36. To this end, a rod 46 is provided for reception into the interior of the piston 38 having an elongated pin 47 extending in an axial direction from the lower end 48 thereof. The pin 47, aperture 44, aperture 33, and the needle 36 are dimensioned with respect to each other such that the pin 47 may project through the apertures 41 and 33 and into the interior of the needle 36. The outer diameter of the pin 47 and the inner diameter of the needle 36 are preferably dimensioned for a minimal clearance therebetween which still allows movement of the pin 47. Since the pin 47 is used to move sample liquid out of the interior of the needle 36, the pin 47 may be said to be displacement means or clearing means.

In the preferred form, a collar 51 is provided coaxially mounted with the rod 46 at the lower end 48 thereof. The collar 51 is dimensioned so that an upper portion of collar 51 receives the rod 46, and a lower portion of the rod 51 receives an end of the pin 47. Radially extending set screws 52 extend through the collar 51 for fastening the rod 46, collar 51 and pin 47 in this relationship. This construction provides for easy replaceability of the pin 47. A coupling member 55 retains the rod 46 in operative engagement with the piston 38. An aperture 56 at an upper end of the member 55 has a larger diameter than the rod 46 and a smaller diameter than the collar 51. The coupling member 55 is placed so that the aperture 56 surrounds a portion of the rod 46, and is provided with a thread 57 on its inner diameter for fastening to the upper end 39 of the piston 38.

Spring biasing means preferably in the form of a spring 59 are provided for insertion in the interior of the piston 38. The spring 59 surrounds the pin 47 and rests between the lower end 40 in the piston 38 and the collar 51, as retained in the piston 38 by the coupling member 55.

Means are provided for coupling vertical force to the rod 46. In the preferred form a rack 61 of teeth is provided extending longitudinally along the rod 46 on the outer surface thereof and parallel to the axis thereof. A pinion 63 is mounted to the housing 17 for coupling motive force to the rod 46. The pinion is driven by a motor 65, mounted on a plate 66 secured to the housing 17, which is operated by control means (not shown). The control means may be operated as described in the above-cited patents to Moran.

When the motor 65 rotates in a first direction, the rod 46 is pulled upwardly. The collar 51 engages the coupling member 55 which pulls the cylinder 38 upwardly. When the motor 65 rotates in the opposite direction, the collar 51 applies force to the spring 59 which is transmitted to the lower end 40 of the cylinder 38. The spring 59 is selected to provide a tensile force such that it does not compress unless the cylinder 38 engages a stop means, e.g. the seating means 32. Therefore, the piston 38 moves down until its lower end 40 engages the stop means. Thereafter, the spring 59 is compressed by the rod 46, and the pin 47 continues its downward travel. Operation is further described below.

In FIG. 4, further details of mounting of the above-described components to the housing 17 are shown. The cylinder 30 is mounted in a block assembly 70 having upper and lower plates 71 and 72, which each have seats formed therein for fixed retaining of the cylinder 30. The lower plate 70 has an aperture therein for permitting communication for an upper end of the needle 36 with the aperture 33 in the lower end of the cylinder 30. Mounting members 75 and 76 are placed on either side of the cylinder 30 and have the plates 71 and 72 mounted thereto for maintaining the cylinder 30 in place. The mounting members 75 and 76 are positioned with respect to the plate 66 to which the motor 65 is mounted so that the axes of the rod 46, pin 47 piston 38, cylinder 30 lie in one line.

OPERATION

Figure 7:
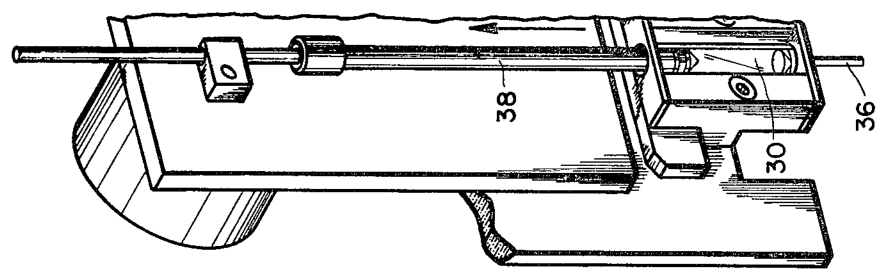
Figure 6:
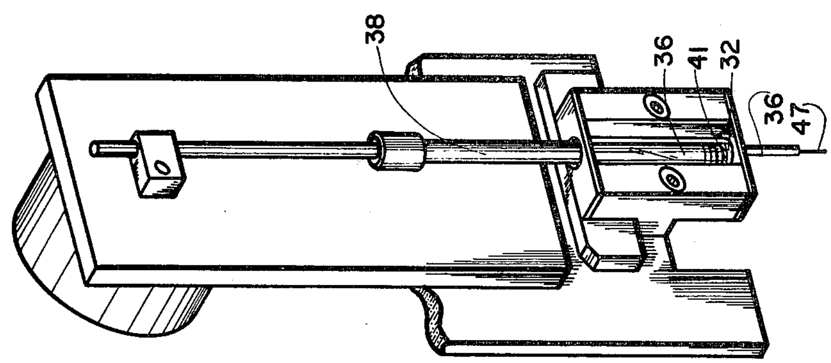
Figure 5:
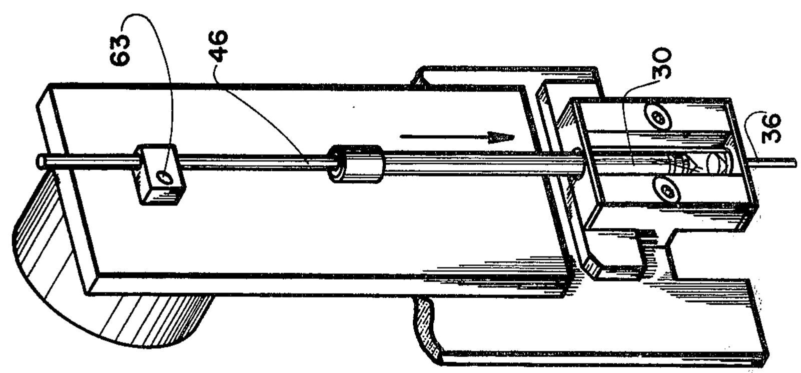

Operation of the transfer means 4 is described with respect to FIGS. 4 through 7. FIGS. 5, 6 and 7 are also axonometric views of the transfer means 4 having the housing 17 broken away to show further details. In FIGS. 5 to 7, the same reference numerals are used to denote elements corresponding to those of FIGS. 1 to 4.

FIGS. 5–7 illustrate a fluid transfer cycle comprising the steps of aspirating sample liquid from one sample container 19, dispensing sample liquid, clearing the cylinder 30 and the needle 36 and preparing for aspirating from a next sample container 19.

Referring now to FIG. 4, at the beginning of an operating cycle, a sample container 19 in the sample conveyor 2 is indexed to the aspiration station 3. The transfer means 4 is moved to the position shown in dotted lines at the right side of FIG. 2. Relative motion is provided between the sample container 19 and the needle 36 so that the lower end of the needle 36 is in communication with sample liquid. In the present embodiment, the drive means 23 drives the rod 24 to push the sample container 19 up so that the sample fluid surrounds the lower end of the needle 36. Prior to projection of the needle 36 into the sample liquid, the pinion 63 may be rotated to lift the rod 46 and piston 38 from a home position in which the lower end 40 of the pistion 38 abuts the seating means 32 of the cylinder 30.

Once the sample liquid is in communication with the lower end of the needle 36, as the piston 38 is raised, sample liquid is drawn into the cylinder 30. The control means (not shown) rotates the pinion 63 until the piston 38 reaches a position of upward travel corresponding to a preselected amount of liquid having been drawn into the cylinder 30. At that point, as seen in FIG. 5, the motor 65 and consequently the pinion 63, is commanded to stop. The transfer means 4 begins movement through the path indicated by area 16 in FIG. 2, and the motor 65 is commanded to rotate in the opposite direction. The piston 38 is moved downwardly as the transfer means 4 moves over the particular slat 20 for dispensing aliquots of liquid to reaction containers 21 therein. During this portion of an operating cycle, the transfer means 4 moves from right to left as seen in FIG. 2 and then from left to right. Dispensing may take place during travel of the transfer means 4 in either or both directions.

After the dispensing operation, the transfer means 4 returns to the aspiration station 3 and is preferably placed over the same reaction container 19 again (FIG. 6). At this time, the motor 65 is rotated to drive the rod 46 and piston 38 to force all remaining liquid out of the cylinder 30. The lower end 40 of the piston 38 presses against the seating means 32 to flush out substantially all remaining liquid from the cylinder 30. The pinion 63 continues rotation. The lower end 40 of the piston 38 is abutting stop means in the form of the seating means 32. The pin 47 therefore continues its travel through the aperture 41 in the lower end 40 of the piston 38 and through the aperture 33 at the lower end of the cylinder 30 through the interior of the needle 36. Virtually all liquid remaining in the needle 36 is forced out. A bead of liquid may form at the lower end of the needle 36 and pin 47. The drive means 23 may be again operated to raise and lower the sample container 19 so that the drop remaining at the lower end of the pin 47 and needle 36 is drawn into the remaining liquid in the sample container 19. The sample container 19 is then lowered to a position in which it is free of engagement with, i.e. no longer surrounding, the needle 36. Liquid remaining on the exterior of the needle 36 will be cleared onto the meniscus of a sample in a next sample container 19 from which sample is aspirated in a next cycle. Since the needle 36 aspirates liquid from a point below the meniscus, carryover will not result from this clearing.

After this portion of the operating cycle, the pinion 53 is again rotated to draw up the rod 46 such that the pin 47 is drawn back into the piston 38. The transfer means 4 is thus enabled to aspirate from a next sample container 12 and resume the operation as illustrated in FIG. 7.

What is thus provided is an improved fluid transfer means in an automatic chemical testing apparatus in which a conduit and reservoir for intermediate storage of sample liquid being transferred from a sample source to reaction containers are cleared by displacement of a solid object therethrough. The ability to prevent carryover without the need for provision of a washing step in which liquid is pumped through the reservoir and conduit is facilitated. This results in simplification of manufacture of the testing apparatus and also avoids the possibility of washing liquid diluting a next sample. The specification has been written with a view toward enabling those skilled in the art to make many modifications from the specific embodiment shown, provide a transfer means in an automatic chemical testing apparatus in accordance with the present invention.

What is claimed as new and desired to be secured by Letters Patent of the United States is:

1. In an automatic chemical testing apparatus including sample liquid transfer means comprising a piston and cylinder communicating with a conduit, said conduit having a lower end for communication with a liquid sample source and an upper end for communication with said cylinder, the improvement wherein said piston and cylinder each comprise an aperture in registration with said conduit and further comprising solid clearing means movable concurrently with or selectively independently of said piston and movable through an interior portion of said piston axially through said apertures and through said conduit for displacement of fluid from said conduit.

2. The improvement according to claim 1 wherein said piston and cylinder are mounted to a transfer means housing and further comprising drive means mounted to said housing, connecting means connecting said drive means to said solid clearing means mounted for axial reciprocal motion with respect to said cylinder.

3. The improvement according to claim 2 wherein said connecting means and said solid clearing means respectively comprise a rod and a pin projecting axially from a lower end of said rod, and wherein said piston is hollow and receives said rod and said pin and wherein said pin projects in said aperture in said piston.

4. The improvement according to claim 3 comprising spring biasing means mounted between said rod and a lower end of said piston in the interior thereof and wherein said rod is mounted to trasmit driving force to said piston through said biasing means when said rod is moved in a first direction, whereby said rod drives said piston in the first direction until said piston abuts stop means and whereby said pin continues to move with respect to said cylinder thereafter.

5. The improvement according to claim 4 further comprising coupling means for transmitting force from said rod to said piston when said rod is moved in an opposite direction.

6. In an automatic chemical testing apparatus having sample liquid transfer means including a reservoir for holding sample liquid which is aspirated into and dispensed from said reservoir, pumping means for moving liquid into or out of said reservoir and a conduit connected to said reservoir for communication with a source of sample liquid, the improvement comprising solid clearing means movably mounted in said pumping means and movable through said conduit for displacing fluid therefrom and means for moving said solid clearing means through said conduit and for providing relative motion between said pumping means and said solid clearing means.

7. The improvement according to claim 6 wherein said means for moving comprises means for providing reciprocal motion such that the solid clearing means is moved in a first direction to displace fluid from said conduit and moved in a second direction to be withdrawn out of said conduit.

8. In an automatic chemical testing apparatus the improvement of a sample liquid transfer apparatus comprising a housing, a reservoir mounted to said housing, a conduit having a first end connected to said reservoir and a second end serving as an inlet and outlet, means for pumping liquid into and out of said reservoir, and solid clearing means movably mounted in said means for pumping and reciprocally movable between a position out of said conduit and a position filling said conduit, for displacing liquid therefrom and means for moving said solid clearing means through said conduit thereby providing relative motion between the means for pumping liquid and said solid clearing means.

9. The improvement according to claim 8 wherein said reservoir comprises a cylinder and said pumping means comprises a piston movable in said cylinder and wherein said solid clearing means is mounted for reciprocal movement out of and into said piston.

10. The improvement according to claim 9 wherein said piston is formed for receiving in its interior an elongated pin comprising said solid clearing means.

11. The improvement according to claim 10 further comprising spring biasing means mounted for biasing said pin such that when said rod moves in a first direction said pin remains in said cylinder and said piston is forced downwardly, said pin is forced through said conduit after said piston engages said stop means at the lower end of said cylinder and wherein said rod is coupled to force to said piston to move said piston upwardly after said pin is retracted into said piston.

12. The improvement according to claim 11 further comprising a rod and a collar and wherein said pin and said rod are connected by said collar such that said pin projects axially from a lower end of said rod and further comprising coupling means mounted to said piston for retaining said collar within said piston whereby said rod may couple said pin to driving means.

13. The improvement according to claim 12 wherein said spring biasing means is mounted in the interior of said piston between a lower end thereof and said collar.

14. The improvement according to claim 13 wherein said conduit comprises a hollow needle and wherein said piston is formed to have a lower end to mate with a seat in a lower end of said cylinder, whereby substantially all fluid is displaced from said reservoir when said piston is seated against said seating means.

15. Apparatus according to claim 14 further comprising means for moving a sample container with respect to said conduit so the lower end of said conduit is placed in sample liquid and maintaining said sample container in that position while said pin is within said piston and said piston is operated to aspirate liquid into the cylinder and movable out of engagement with said conduit thereafter.

16. Apparatus according to claim 15 further comprising means for moving said sample container relative to said needle when said pin projects from said needle such that the lower end of said needle and said pin are dipped into said sample liquid, whereby a meniscus of the liquid in said sample container clears any drops from said pin and said needle.

17. Apparatus according to claim 16 comprising a mounting block mounting said cylinder to a wall of a housing of said sample liquid transfer apparatus.

18. Apparatus according to claim 9 further comprising means for moving a sample container relative to said conduit when said clearing means projects from said conduit such that the lower end of said conduit and said clearing means are dipped into said sample liquid, whereby a meniscus of the liquid in said sample container clears any drops from said clearing means and said conduit.

19. The improvement according to claim 14 wherein said drive means comprises a rack formed on the exterior of said rod parallel to the axis thereof and a pinion meshing with said rack and a motor for driving said pinion.

* * * * *